United States Patent [19]

Diers

[11] 4,042,460

[45] Aug. 16, 1977

[54] METHOD FOR PRODUCING GLUCOSE ISOMERASE

[75] Inventor: Ivan Verner Diers, Lille Vaerlose, Denmark

[73] Assignee: Novo Industri A/S, Bagsvaerd, Denmark

[21] Appl. No.: 706,991

[22] Filed: July 20, 1976

[30] Foreign Application Priority Data

July 22, 1975 United Kingdom ............... 30693/75

[51] Int. Cl.$^2$ ............................................. C12D 13/10
[52] U.S. Cl. ..................................... 195/65; 195/109; 195/115
[58] Field of Search .............. 195/65, 109, 66 R, 31 F

[56] References Cited

U.S. PATENT DOCUMENTS

| 3,826,714 | 7/1974 | Suekane et al. | 195/31 F |
| 3,956,066 | 5/1974 | Coker et al. | 195/31 F |

*Primary Examiner*—Lionel M. Shapiro
*Attorney, Agent, or Firm*—Fidelman, Wolffe & Waldron

[57] ABSTRACT

Production of glucose isomerase from facultative aerobic microorganisms by limiting oxygen supply to growth-limiting amounts in the presence of excess glucose and other nutrients in sufficient amounts.

Enzyme yield from oxygen growth-limiting proportions is superior to yields obtained from glucose growth-limiting circumstances.

9 Claims, No Drawings

METHOD FOR PRODUCING GLUCOSE ISOMERASE

The present invention is concerned with a process for production of a glucose isomerase product by continuous fermentation.

BACKGROUND OF THE INVENTION

Syrups containing a mixture of glucose and fructose are widely used in industry because of their sweet taste and their low tendency to crystallize. Such syrups are commonly produced from glucose syrups using a glucose isomerase to catalyze the isomerization of glucose to fructose. Important for the economy of this process are low enzyme costs and negligible formation of by-products, that must be removed before the syrup can be used.

Glucose isomerases may be obtained from a large number of different species of microorganisms, and the properties of the glucose isomerases vary from species to species.

Once the microorganism for production of glucose isomerase has been selected it is of the utmost importance to carry out enzyme production in such a way that the enzyme cost is as low as possible. The enzyme cost is largely dependent upon the cost of the fermentor and upon the details of how the fermentation is carried out therein, notably the cost of the materials in the fermentation medium, the fermentation time, the power requirement, the concentration of enzyme in the fermentation broth and the yield of enzyme. In this connection it should be noted that production of many enzymes involved in catabolism of microorganisms e.g. glucose isomerase, are known to be reduced by presence of glucose and other energy rich compounds in the fermentation medium, the expression "repression" being used hereafter to identify the phenomenon of enzyme yield suppression by growth conditions. Thus, in order to get a better yield of glucose isomerase, other carbon sources than glucose could be used, e.g., glycerol, or alternatively the glucose content in the fermentation medium be controlled to growth-limiting concentrations.

Carbon limited growth can be carried out in three preferred ways. One is the dosed batch fermentation wherein a carbon and energy source is supplied to a batch culture in the post-log phase at a constant rate, which limits growth and relieves repression on enzyme synthesis. Another method is a fed batch fermentation (Pirt, S. J. (1974), J. appl. Chem. Biotechnol. 24, 415). A fed batch fermentation can be a homogeneous batch fermentation which is growth limited by the concentration of the carbon and energy source, where all other nutrients are present in excess. When the growth-limiting carbon and energy source is exhausted, the batch culture is supplied continuously with nutrient medium. Fermentation broth is removed discontinuously. The volume variation and the discontinuous removal of fermentation broth distinguishes the fed batch fermentation from a chemostat culture. Finally (and most efficiently) carbon limited growth can be carried out in the classical chemostat (Monod, J., A. Rev. Microbiol., 3, 64 (1949)). A chemostat culture consists of a perfectly mixed suspension of biomass into which medium is fed at a constant rate (F), and the culture is removed from the chemostat at the same rate, the volume of the culture (V) thus remains constant. In steady state the ratio $F/V = D$ (dilution rate) is equal to the specific growth rate $\mu$. Using this technique e.g. Smith and Dean (J. Gen. Microbiology 72, 37-47 (1972)) found an increased yield of beta-galactosidase in lactose (the carbon and energy source) limited chemostat cultures of Klebsiella aerogenes.

During fermentation of glucose isomerase producing microorganisms, any growth-limitation due to oxygen is usually avoided. Thus normally a sufficient amount of air is supplied to the medium, or the fermentation is operated with growth-limiting factors other than oxygen, e.g. a growth-limitation due to a nutrient. Growth-limitation due to oxygen is unwanted because then carbon sources in excess will be repressing enzyme production.

Since the saturation concentration of oxygen in fermentation media is very low, conventional fermentors designed to the fermentation of glucose isomerase are constructed in a manner which provides a high transfer rate of oxygen from the gaseous phase to the liquid phase. Conventional fermentors for glucose isomerase fermentation thus are constructed with agitators designed to a high rotational velocity and/or with an efficient distributor means from the air intake and/or with an air intake with a high capacity of air blown into the fermentor per unit of time and/or with a fermentor design having a high ratio between height and width. The oxygen concentration in the fermentation medium might well be very low but still not be growth-limiting, due to the high transfer rate of oxygen from the gaseous phase to the liquid phase.

The concentration of oxygen in the fermentation medium is measured according to a polarographic or galvanic measuring method. The sensitivity of these methods is rather small; oxygen concentrations below 1.5 mm Hg can only be detected with difficulty in large scale operation.

BRIEF DESCRIPTION OF THE INVENTION

Now, according to this invention, it has been found that an increase in the yield of glucose isomerase can be obtained if the fermentation is carried out with a supply of oxygen which is growth-limiting, if facultative aerobic microorganisms are used and if certain other operating conditions are adhered to.

More specifically the process for production of a glucose isomerase product by fermentation according to the invention comprises the fermentation of a facultative aerobic, glucose isomerase producing microorganism with a supply of oxygen which is growth-limiting, and a carbon and energy source which represses glucose isomerase synthesis and which is easily converted anaerobically to non repressing degradation products such as glucose is added in a slight excess and all other nutrients are added in sufficient amounts, the glucose isomerase product is, of course, recovered in due course.

Thus according to the invention a very high yield of glucose isomerase is produced; furthermore the power requirement is reduced due to the fact that a smaller supply of oxygen is introduced; as a result the overall cost of the glucose isomerase produced according to the invention is lowered.

DETAILED DESCRIPTION OF THE INVENTION

Thus the invention is limited to the use of glucose isomerase producing microorganisms of a facultative aerobic nature. By supplying the oxygen in an amount which is growth-limiting a condition is established in which the facultative aerobic bacteria are growing partially anaerobic, partially aerobic. It is believed that in some way or another this special condition is connected with the high yields of glucose isomerase obtained. The microorganism can be any facultative aerobic, glucose isomerase producing microorganism. *Bacillus coagulans* and the atypical *Bacillus coagulans* described in Ser. No. 428,682 filed Dec. 27, 1973 are preferred microorganisms according to the invention.

Although the fermentation is carried out with a supply of oxygen which is growth-limiting, the weight of cell mass provided by the aerobic metabolism is many times larger than the weight of cell mass provided by the anaerobic or fermentative metabolism. Apparently, therefore an aerobic metabolism should be preferred over anaerobic metabolism but it has been found that the very high yields or glucose isomerase desired cannot be obtained, unless the growth process involves both aerobic and anaerobic metabolism.

According to the invention the fermentation medium has added thereto a source of carbon and energy which represses glucose isomerase synthesis and which is easily converted anaerobically to non-repressing degradation products in a slight excess is also necessary to achieve the high yields of glucose isomerase. The carbon and energy source can be any carbon and energy source of the specified kind, mainly carbohydrates inclusive of hydrolyzed starch, and especially hexoses and pentoses. Among the hexoses especially glucose and fructose are preferred. Among the pentoses especially xylose and ribose are preferred. All other nutrients are added in sufficient quanties i.e. in quantities that do not limit growth.

The glucose isomerase product is recovered from the fermentation broth, in a conventional manner.

A preferred embodiment of the process for production of a glucose isomerase product according to the invention comprises the use of *Bacillus coagulans* as the glucose isomerase producing microorganism.

A preferred embodiment of the process for production of a glucose isomerase product according to the invention comprises the use of an atypical *Bacillus coagulans* described by U.S. patent application Ser. No. 428,682 filed Dec. 27, 1973 as the glucose isomerase producing microorganism. The atypical *B. coagulans* productive of glucose isomerase is characterized by being cable of growth under aerobic conditions on only inorganic nitrogen sources and at a temperature of 65° C.

A preferred embodiment of the process for production of a glucose isomerase product according to the invention comprises the use of a constitutive and asporogenic mutant of an atypical *Bacillus coagulans* mutated and recovered as described by Example IV of U.S. Ser. No. 428,682, now U.S. Pat. No. 3,979,261, for the glucose isomerase producing microorganism.

A preferred embodiment of the process for production of a glucose isomerase product according to the invention comprises the use of continuous fermentation.

A preferred embodiment of the process for production of a glucose isomerase product according to the invention comprises the separate addition of the carbon and energy source in controlled amounts.

A preferred embodiment of the process for production of a glucose isomerase product according to the invention comprises a continuous fermentation, wherein the dilution rate has a value between 0.05 and 0.20.

A preferred embodiment of the process for production of a glucose isomerase product according to the invention comprises the use of a dosed batch fermentation where the carbon source is added separately. A preferred embodiment of the process for production of a glucose isomerase product according to the invention comprises the use of glucose, hydrolyzed starch or xylose as a carbon source.

The process according to the invention can be carried out both batchwise, as a fed batch fermentation or as a dosed batch fermentation and continuously, and in all cases high yields are obtained. The continuous process can be carried out according to a pH-static principle, where the source of carbon and energy is added separately, when pH exceeds the set point. In the continuous process the dilution rate should be rather low and preferably corresponding to the levels productive of optimum enzyme yield. The medium in which the fermentation is carried out is conventional, except for the above described limitations on the composition thereof. The carbon and energy source is present in a slight excess, desirably from 1–20% excess, and all the other nutrients in the medium, viz. N,P,S and Mg are added in sufficient amounts. Thus, the medium is a conventional mineral salts medium which can be enriched with an organic nitrogen source as yeast extract, corn steep liquor or similar N sources, plus a carbon and energy source which, of course, can be one of the earlier mentioned, e.g. glucose.

Since the carbon and energy source, which normally would be a carbohydrate, including for example glucose and hydrolyzed starch, are expensive ingredients, the carbon and energy source constitutes a convenient nutrient for growth-limiting purposes. Its characteristic of repressing enzyme growth when in excess (of growth-limiting quantities) makes control of the glucose content that much more important to efficient production of glucose isomerase. In terms of this invention, the 1–20% excess glucose alluded to above is with reference to the glucose content in the nutrient allowable for the glucose to be growth-limiting in the fermentation system employed. Allusion to the other nutrients as being present in the medium in sufficient quantity references, of course, non-growth limiting proportions.

Since all other nutrients are in some degree of excess, the most limiting factor is the oxygen present in the fermentation broth. Manifestly, introduction of excess oxygen would make glucose the growth limiting ingredient. On the other hand, severe oxygen starvation conditions result in low yield of microorganism cells (in grams per gram of glucose) and little or no enzyme yield. As the oxygen introduced into the fermentation broth approaches the quantity usable for nutrient purposes from either excess or starvation amounts, both biomass and enzyme yield increase. The peak yields have been found to occur at about near zero in measurable partial pressure of oxygen in solution. This near zero oxygen condition involves then introduction of the most oxygen that can be consumed by the microorganism without leaving enough free oxygen in solutions for polarographic or galvanic detection. In practice maintenance of a barely measureable partial pressure of oxygen will ensure high enzyme yields.

As the supply of oxygen to the fermentation medium is intended to be the growth-limiting factor it is carefully adjusted to maintain the partial pressure of dissolved oxygen in the fermentation medium close to zero. This condition can be established by adding a current of air to the fermentor and reduce the rotational speed of the agatator until the partial pressure of the dissolved oxygen decreases to the near to zero value. Also this near zero oxygen condition can be established by adjusting the velocity of air supply when the stirrer revolves with a constant speed, or by diluting the air with varying amounts of an inert gas, e.g. $N_2$.

The following examples are given for the purpose of illustrating the present invention.

In all the examples the same microorganism is used. This microorganism is a constitutive and asporogenic mutant originating from the atypical *Bacillus coagulans* NRRL 5650. The mutation is carried out as described in the U.S. patent application Ser. No. 428,682, Example IV, "Isolation of mutant bacteria which are able to produce glucose isomerizing activity in xylosefree media".

EXAMPLE I

In all experiments in this example a 1 liter BIOFLO C30 fermentor from New Brunswick Sci. Inst., New Brunswick, N.J., USA with a operative volume capacity of 300–350 cm³ was used.

The rotational speed of the agitator was varied from 250 to 500 rpm.

pH was adjusted to 7.0 ± 0.2 by means of 1 N NaOH. The temperature was kept at 50° C ± 0.2° C.

The tension of dissolved $O_2$ ($C_{O_2,L}$) was kept at a value, which was practically zero, when $O_2$ was growth-limiting, and in all comparison experiments later referred to the tension of $O_2$ was kept at a value higher than 20 mm Hg. The dilution rate D was approximately the same in all experiments. The medium had the following composition:

TABLE A

| Medium ingredients | Medium Composition, g/l limiting factor | | | | |
|---|---|---|---|---|---|
| | $O_2$ | C | N | P | Mg |
| $(NH_4)SO_4$ | 2.5 | 2.5 | 0.4 | 2.5 | 2.5 |
| $K_2HPO_4$ | 1.0 | 1.0 | 1.0 | 0.021 | 1.0 |
| $NaH_2PO_4 2H_2O$ | 1.0 | 1.0 | 1.0 | 0.021 | 1.0 |
| NaCl | 0.25 | 0.25 | 0.25 | 0.25 | 0.25 |
| $MgSO_4 7H_2O$ | 0.1 | 0.1 | 0.1 | 0.1 | 0.04 |
| $FeCl_3 6H_2O$ | 0.02 | 0.02 | 0.02 | 0.02 | 0.02 |
| $MnSO_4 H_2O$ | 0.02 | 0.02 | 0.02 | 0.02 | 0.02 |
| $ZnSO_4$ | 0.0025 | 0.0025 | 0.0025 | 0.0025 | 0.0025 |
| $CaCl_2$ | 0.0075 | 0.0075 | 0.0075 | 0.0075 | 0.0075 |
| Thiamine.HCl | 0.001 | 0.001 | 0.001 | 0.001 | 0.001 |
| Glucose | 8 | 8 | 8 | 8 | 8 |
| EDTA | 0.083 | 0.083 | 0.083 | 0.083 | 0.083 |
| Pluronic H-61 | 0.083 | 0.083 | 0.083 | 0.083 | 0.083 |
| Distilled water | ad 1 l | ad 1 l | ad 1 l | ad 1 l | ad 1 l |

Bacterial dry weight (X) was determined in the following way. A 5 ml sample was centrifuged 10 min. at 5000 rpm, immediately after sampling. The cells were washed once in ice-cold phosphate buffer (0.05% w/v/, pH 6.5, and centrifuged as above. The precipitate was dried at 105° C to constant weight. The relationship between $OD_{450}$ and X was found to deviate less than 10% from 0.35 mg dry weight cell per $OD_{450}$ unit.

The glucose isomerase assay was carried out in the following way. The sample was diluted in maleate buffer (0.25 M maleic acid, 0.10M $MgSO_4$, $7H_2O$, 0.475 M NaOH and 1.0% w/v KCE; pH 6.5) and then treated with lysozyme for total release of enzyme from the microorganism cells. To 1 ml sample was added 0.1 ml of a solution of eggwhite lysozyme (Sigma Chemicals), corresponding to 44.000 units. After 1 hour of lysozyme treatment, glucose substrate (1 ml 0.278 M glucose and 0.001 M $CoCl_2$. $6H_2O$) was added and isomerization carried out for 20 min. at 65° C. The reaction was stopped by addition of 10 ml 0.1 M perchloric acid. 0.5 ml of the isomerate was used for the colour reaction with cysteine-carbazole-sulphuric acid. First 0.1 ml 1-cysteinium chloride (2.2% w/v) freshly made was added. Then 3 ml of a mixture of 1 ml carbazole solution (0.4 w/v in ethanol) and sulphuric acid (80% w/v in water). The violet colour was measured at 560 nm after development for 30 min. at 30° C. Running blanks of substrate as well as sample were absolutely necessary. One unit of glucose isomerase was defined as the amount of enzyme which catalyzes the formation of 1 μmole fructose per minute at the conditions of the reaction.

The organism was cultivated continuously with a supply of $O_2$ which is growth-limiting. Also, for comparative reasons, similar continuous cultivations were carried out with supplies of C, N, Mg and P, which were growth-limiting individually. Cell mass and enzyme production were investigated and related to the fermentation conditions, and especially the results in connection with the fermentations where $O_2$ and C were growth-limiting were investigated.

The results of these experiments are summarized in the following table.

TABLE I

| dilution rate D, $hr^{-1}$ | limiting factor | yield of cell mass, mg dry weight bacteria/mg glucose | enzyme yield glucose isomerase units/mg dry weight bacteria | Productivity, glucose isomerase units/mg glucose hour |
|---|---|---|---|---|
| 0.12 | $O_2$ | 0.17 | 0.98 | $2.00 \times 10^{-2}$ |
| 0.12 | C | 0.29 | 0.38 | $1.16 \times 10^{-2}$ |
| 0.13 | N | 0.09 | 0.06 | $0.07 \times 10^{-2}$ |
| 0.11 | P | 0.09 | 0.17 | $0.17 \times 10^{-2}$ |
| 0.10 | Mg | 0.175 | 0.11 | $0.19 \times 10^{-2}$ |

It appears from the above table that the condition where $O_2$ is growth-limiting creates by far the best enzyme yield and highest productivity.

EXAMPLE II

The same fermentor as described in example 1 was used in this example on fed batch fermentation. The stirrer speed was 350 rpm throughout the experiment, and the volume varied from 150 mls to 350 mls. pH was adjusted to 7.0 ± 0.2 with 1 N NaOH. The temperature was adjusted to 50° C ± 0.2° C.

The composition of medium was as follows:

| $(NH_4)SO_4$ | 3 g per l |
|---|---|
| Difco yeast extract | 10 g per l |
| $K_2HPO_4$ | 1 g per l |
| $MgSO_4 . 7H_2O$ | 0.5 g per l |
| Tap water to | 1 liter |

After sterilization at 130° C in 60 min. 10 grams of glucose was added aseptically to the medium.

Procedure of cultivation and results:

The fermentor was inoculated from a fresh nutrient broth culture (0.5 mls into 150 mls of the medium). After a short lag-phase batch growth started and 17 hours later medium was supplied with a constant rate of 27.6 mls/hour; 8 hours later the fermentor volume was filled up and the experiment finished. Throughout the dosage period the oxygen tension exhibited a measured value of zero. Biomass and enzyme yield was determined as in example 1.

| Results: | yield of a biomass: | 3.56 g per l |
| --- | --- | --- |
| | yield of enzyme: | 4.1 glucose isomerase units per ml. |

EXAMPLE III

In this example a 10 l (operative volume) Biotec fermentor FL 110, Biotec, Bromma, Sweden, was used. Air was sparged into the bottom of the fermentor with a constant rate of 10 l/min, the stirrer speed was kept at 620 rpm and the temperature at 50° C. The vessel was inoculated from an *o/n* nutrient agar slant. The medium consisted of:

| Corn steep liquor (50% dry weight) | 30 g per l |
| --- | --- |
| $K_2HPO_4$ | 1.5 g per l |
| $(NH_4)_2SO_4$ | 5 g per l |
| glucose | 2 g per l |
| $MgSO_4 \cdot 7H_2O$ | 0.1 g per l |
| $MnSO_4 \cdot HO_2$ | 0.05 g per l |
| Pluronic H-61 | 0.3 g per l |
| meutralized to pH 6.8 with 30% sodium hydroxide | |
| Tap water to | 1 liter |
| sterilized at 121° C for 105 minutes | |

13 hours after inoculation batch growth terminated and pH began to increase; the measured value of the oxygen tension in the medium was now zero. When pH reached 6.5 40% glucose solution was added via the pH-meter/titrator and a peristaltic pump; in this way pH was kept constant through the next 8 hours, and glucose was supplied with a constant rate of 2.1 g/l × hour; at the end of this period the oxygen tension increased from a measured value of zero to a measured value higher than zero, and growth terminated again. Cells were harvested and biomass and enzyme yield determined as above.

| Results: | Yield of Biomass: | 4.2 g per l |
| --- | --- | --- |
| | Yield of enzyme: | 8.8 glucose isomerase units/ml. |

What is claimed is:

1. Process for production of a glucose isomerase product by fermentation, which process comprises the fermentation of a facultative aerobic, glucose isomerase producing microorganism with a supply of oxygen which is growth-limiting, and with a source of carbon and energy which represses glucose isomerase synthesis yet is readily converted anaerobically to non repressing degradation products added in slight excess and all other nutrients are added in sufficient amounts, and thereafter recovering the glucose isomerase product.

2. Process for production of a glucose isomerase product according to claim 1, wherein a glucose isomerase strain of *Bacillus coagulans* is used as the glucose isomerase producing microorganism.

3. Process for production of a glucose isomerase product according to claim 2, wherein the *Bacillus coagulans* is an atypical strain characterized by growth on only inorganic sources of nitrogen and by an ability to grow at 65° C.

4. Process for production of a glucose isomerase product according to claim 1 wherein the fermentation medium has therein from 1-20% excess glucose as the source of carbon and energy.

5. Process for production of a glucose isomerase product according to claim 1 wherein the process is carried out as a continuous fermentation.

6. Process for production of a glucose isomerase product according to claim 5, wherein the carbon and energy source is added separately from other nutrients.

7. Process for production of a glucose isomerase product according to claim 5, wherein the dilution rate has a value between 0.05 and 0.20.

8. Process for production of a glucose isomerase product according to claim 1, wherein the glucose isomerase is produced by means of a dosed batch fermentation and wherein the carbon and energy source is added separately from the other nutrients.

9. Process for production of a glucose isomerase product according to claim 1, wherein glucose, hydrolyzed starch or xylose is used as the carbon and energy source.

* * * * *